US005756821A

United States Patent [19]
Dilk et al.

[11] Patent Number: 5,756,821
[45] Date of Patent: May 26, 1998

[54] OPEN-CHAIN OLEFINICALLY UNSATURATED COMPOUNDS, PROCESSES FOR THEIR PREPARATION AND THEIR USE AS AROMA SUBSTANCES

[75] Inventors: Erich Dilk; Peter Wörner, both of Holzminden, Germany

[73] Assignee: Haarmann & Reimer GmbH, Holzminden, Germany

[21] Appl. No.: 706,079

[22] Filed: Aug. 30, 1996

[30] Foreign Application Priority Data

Sep. 6, 1995 [DE] Germany ............ 195 32 886.8

[51] Int. Cl.$^6$ .................................... C07C 69/00
[52] U.S. Cl. .................................... 560/129
[58] Field of Search .................... 568/875, 876, 568/880; 560/129

[56] References Cited

U.S. PATENT DOCUMENTS 3,296,080  1/1967  Meuly et al. .
3,668,255  6/1972  Meuly et al. .

FOREIGN PATENT DOCUMENTS 06092884  4/1994  Japan .

OTHER PUBLICATIONS

Dillenberger et al., Helv. Chim. Acta (1978), 61(5), 1856–902.
Hendrickson et al., Organic Chemistry, 1970, p. 459.
Organikum, p. 402 et seq.
Houben–Weyl, p. 659, et seq.
Chemical Abstracts, vol. 121, NO. 17, Columbus, Ohio, US; abstract No. 205745, XP002018943 *das ganze Dokument* & JP-A-06 092 884 (Kuraray), (Oct. 24, 1994).
T.A. Rudolfi, et al., Gas Chromatographic Behaviour of Fragrances on Apiezon L and 1,2,3–tris(ss–Cyanoethoxy)propane, Journal of Chromatography, 365, pp. 429–434, (1986).
H. Mayr, et al., Synthesis of 2,2,5,5–Tetramethylcyclopentanecarboxylic Acid—A Building Block of an Amino Acid Based Sweetener, Chem. Ber., 124, pp. 203–206, (1991).
Chemical Abstracts, vol. 98, No. 10, Columbus, Ohio, US; abstract No. 77949, XP002018941 *Zusammenfassung*, *RN:84607–59–0* & SU-A-960 157 (Inst. of Chemistry), (Mar. 7, 1993).
STN Information Service, File: Registry, XP002018940 *RN:94087–22–6*.
Chemical Abstracts, vol. 90, No. 1, Columbus, Ohio, US abstract No. 5496, XP002018942 *RN:67682–18–2* *Zusammenfassung* (Jan. 1, 1979) & Helv. Chem. Acta, Bd. 61, No. 5, Seiten 1856–18902 (1978).
Dillenberger, et al.: "Studies on the Migratory Aptitude of Allyl Groups in Aliphatic Carbenium Ions".

Primary Examiner—Gary Geist
Assistant Examiner—Karl J. Puttlitz, Jr.
Attorney, Agent, or Firm—Sprung Kramer Schaefer & Briscoe

[57] ABSTRACT

Open-chain branched olefinically unsaturated alcohols and esters are excellent aroma substances.

3 Claims, No Drawings

OPEN-CHAIN OLEFINICALLY UNSATURATED COMPOUNDS, PROCESSES FOR THEIR PREPARATION AND THEIR USE AS AROMA SUBSTANCES

The invention relates to open-chain branched olefinically unsaturated alcohols and esters, two processes for their preparation and their use as aroma substances.

Because of the generally inadequate availability of many naturally occurring components of aroma substances, the need to adapt to changing directions in fashion tastes and the constantly increasing demand for new aroma substances which, by themselves or in the form of compositions, are valuable perfumes or fragrances having interesting fragrance notes, there is still a need for new compounds having valuable aroma substance qualities.

Surprisingly, it has been found that certain open-chain branched olefinically unsaturated alcohols and esters—preferably those of the type of trimethylhexene, trimethylheptene and tetramethyloctene compounds—have outstanding aroma substance properties.

The invention thus relates to compounds of the formula

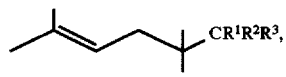

wherein
$R^1$ denotes $$-OH, -OCH \overset{O}{\underset{\|}{}} \text{ or } -OC\overset{O}{\underset{\|}{}}-C_1-C_6\text{-alkyl},$$

preferably $$-OH, -OCH \overset{O}{\underset{\|}{}} \text{ or } -OC\overset{O}{\underset{\|}{}}-C_1-C_4\text{-alkyl},$$

$R^2$ denotes hydrogen or $C_1-C_6$-alkyl, preferably hydrogen or $C_1-C_4$-alkyl, and $R^3$ denotes hydrogen, $C_1-C_4$-alkyl or vinyl, preferably methyl or isopropyl, with the proviso that $R^2$ and $R^3$ do not simultaneously represent hydrogen if $R^1$ denotes hydroxyl.

The alcohols (I) can be prepared by reaction of the corresponding carbonyl compounds, preferably, that is to say, the aldehydes or ketones, with organometallic alkylating agents, such as, for example, butyllithium or Grignard compounds $R^2MgX$ or $R^3MgX$ (X=halogen from the series consisting of chlorine, bromine and iodine):

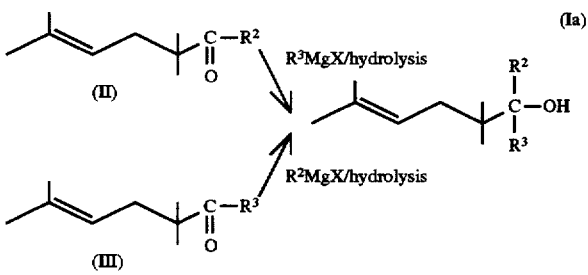

The organometallic alkylating agents are in general employed in at least equivalent amounts, based on the carbonyl compound (II) or (III).

The reactions are as a rule carried out in an organic solvent which is inert under the reaction conditions. Suitable inert solvents include, above all, ethers, such as, for example, diethyl ether, dibutyl ether, ethylene glycol dimethyl and dibutyl ether, anisole and tetrahydrofuran. However, for example, hydrocarbons, such as hexane, are also suitable.

The reactions are in general carried out at temperatures from 20° to 80°, preferably 20° to 65° C. When the reaction and hydrolysis have ended, the alcohol formed can be extracted from the aqueous phase by means of an organic solvent which is immiscible with water.

The invention thus relates to a process for the preparation of the alcohols (Ia) by reaction of the carbonyl compounds (II) or (III) with an organometallic compound $R^2$—Y or $R^3$—Y, wherein Y represents Li or MgX and X represents halogen from the series consisting of chlorine, bromine and iodine.

The alcohols (I) can also be prepared by reduction of the corresponding carbonyl compounds, preferably, that is to say, the aldehydes or ketones, but also the esters, acid chlorides or carboxylic acids, with complex hydrides, such as, for example, sodium borohydride, lithium aluminium hydride or lithium borohydride.

The reduction is in general carried out by employing at least the amount of complex hydride necessary for complete conversion, thus in the case of reduction of aldehydes and ketones 0.25 mol, for esters and acid chlorides 0.5 mol and for carboxylic acids 0.75 mol of complex hydride. The reduction can also proceed as follows:

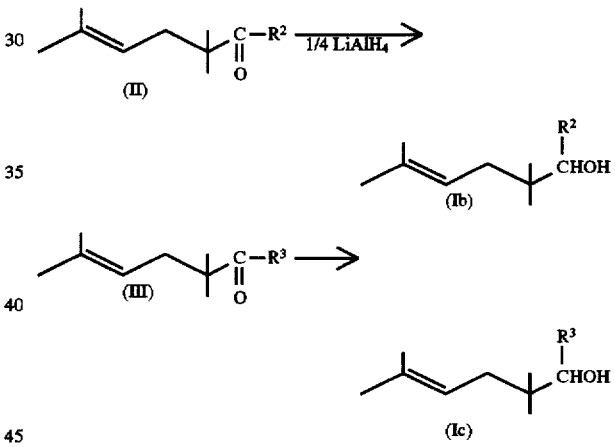

The reduction can be carried out in inert organic solvents such as are mentioned above for the reaction with organometallic reagents. The reactions can be carried out at temperatures of 20° to 90°, preferably 20° to 65° C. After the hydrolysis, working up can be carried out in the customary manner.

The invention thus also relates to a process for the preparation of the alcohols (I) or (Ic) by reduction of the carbonyl compounds (II) or (III) with a complex hydride.

The carbonyl compounds to be used as starting compounds for the two processes according to the invention which have been described are known (for example from U.S. Pat. No. 3,668,255 or H. Mayretal., Chemische Berichte 124 (1991), pages 203–206, VCH Verlagsgesellschaft mbH, Weinheim), or they can be prepared by processes analogous to those known from the prior art.

If required, the corresponding esters can be prepared from the alcohols (I). The customary esterification methods can be used for this, such as are described, for example, in "Organikum", Deutscher Verlag der Wissenschaften, 18th Edition, Berlin 1990, page 402 et seq. and "Methoden der Organischen Chemie [Methods of Organic Chemistry]" (Houben-Weyl), Volume E 5, page 659 et seq., Georg Thieme Verlag, Stuttgart 1985. A preferred process is the reaction of the alcohols with carboxylic acids or carboxylic acid anhydrides, if appropriate in the presence of an esterification catalyst.

Preferred carboxylic acids and carboxylic acid anhydrides are, for example, formic acid, acetic acid, propionic acid, acetic anhydride, propionic anhydride and butyric anhydride.

Preferred esterification catalysts include, for example, phosphoric acid, sulphuric acid, anhydrous hydrochloric acid, sulphonic acids, ion exchangers or sodium acetate.

The invention thus also relates to a process for the preparation of the esters I by esterification of the corresponding alcohols I with carboxylic acids or carboxylic acid anhydrides.

The compounds (I) according to the invention have extremely attractive fragrance notes which are distinguished in particular by freshness and are reminiscent of bergamot, grapefruit and citrus. They can be readily combined with other aroma substances to give interesting compositions, the amount preferably being 1 to 50% by weight, based on the entire composition.

As well as in fine perfumery, such compositions can be used for perfuming cosmetics, such as creams, lotions, aerosols and toilet soaps, and industrial articles, such as cleaning compositions and detergents, softeners, disinfectants and textile treatment agents.

The invention thus also relates to the use of the compounds I as aroma substances.

The percentage data in the following examples in each case relate to the weight.

EXAMPLES

Example 1

2,4,4,7-Tetramethyl-oct-6-en-3-ol 91 g of 2,4,4,7-tetramethyl-oct-6-en-3-one are stirred with 19 g of sodium borohydride in alcohol at 40° C. for 24 hours. The alcohol is distilled off, water is added and the product is extracted with tert-butyl methyl ether. The organic phase is washed neutral and distilled over a 40 cm packed column.

This gives 50.3 g (55% of theory) of product, boiling point$_{10mbar}$=87° C.

Smell: camphor, styryl acetate, green, good adhesion

Example 2

2,3,4,4,7-Pentamethyl-oct-6-en-3-ol 187 g of a 20% strength by weight solution of methylmagnesium chloride in tetrahydrofuran are added dropwise to 91 g of 2,4,4,7-tetramethyl-oct-6-en-3-one at 40° C. in the course of 2 hours. The mixture is then heated under reflux for 4 hours. When the reaction has ended, most of the tetrahydrofuran is distilled off, and ice/hydrochloric acid are added. The product is extracted with tert-butyl methyl ether, washed neutral and distilled over a 30 cm packed column.

82 g (83% of theory) of product of boiling point$_{10mbar}$=96° C. are obtained.

Smell: blackcurrant, camphor, grapefruit, citrus, fresh

Example 3

3-Isopropyl-4,4,7-trimethyl-octa-1,6-dien-3-ol

From 72.8 g of 2,4,4,7-tetramethyl-oct-6-en-3-one and 400 ml of a vinylmagnesium bromide solution (1 mol) analogously to Example 2.

36 g (43% of theory) of product of boiling point$_{10mbar}$=110° C. are obtained.

Smell: tart, camphor, fruit

Example 4

2,4,4,7-Tetramethyl-oct-6-en-3-ol formate 52 g of 2,4,4,7-tetramethyl-oct-6-en-3-ol and 65 g of formic acid are stirred at 40° C. for 8 hours. The formic acid is then distilled off and the product is purified by cracking tube distillation.

This gives 22.7 g (38% of theory) of product of boiling point$_{10mbar}$=118° C.

Smell: bergamot, grapefruit, oil of clary sage, citrus

Example 5

2,4,4,7-Tetramethyl-oct-6-en-3-ol acetate 57.6 g of 2,4,4,7-Tetramethyl-oct-6-en-3-ol and 33.6 g of acetic anhydride are heated under reflux, with the addition of 10 g of sodium acetate, for 5 hours. Water is added, the mixture is extracted with tert-butyl methyl ether and the product is distilled over a 30 cm packed column.

52 g (77% of theory) of product of boiling point$_{10mbar}$=92° C. are obtained.

Smell: fresh, camphor, bergamot, grapefruit

Example 6

2,2,5-Trimethyl-hex-4-en-1-ol formate 92 g of 2,2,5-trimethyl-hex-4-en-1-ol and 130 g of formic acid are stirred at room temperature for 6 hours. 400 ml of water are added, the phases are separated and the product is then distilled.

This gives 87 g (80% of theory) of product of boiling point$_{10mbar}$=49° C.

Smell: grapefruit, fresh, bergamot, styryl acetate, carbinol

Example 7

2,2,5-Trimethyl-hex-4-en-1-ol propionate 49.7 g of 2,2,5-trimethyl-hex-4-en-1-ol, 70 ml of propionic anhydride and 0.1 ml of phosphoric acid are stirred at room temperature. 300 ml of tert-butyl methyl ether are added, the mixture is washed neutral and the organic phase is distilled.

66 g (95% of theory) of product of boiling point$_{10mbar}$=70° C. are obtained.

Smell: fresh, green, bergamot, watery

Example 8

3,3,6-Trimethyl-hept-5-en-2-ol formate

From 46.8 g of 3,3,6-trimethyl-hept-5-en-2-ol and 60 g of formic acid analogously to Example 6.

This gives 34.6 g (63% of theory) of product of boiling point$_{10mbar}$=78° C.

Smell: fresh, styryl acetate, grapefruit, blossom

Example 9

3,3,6-Trimethyl-hept-5-en-2-ol propionate

From 46.8 g of 3,3,6-trimethyl-hept-5-en-2-ol, 70 ml of propionic anhydride and 0.1 ml of phosphoric acid analogously to Example 7.

52.6 g (82.3% of theory) of product of boiling point$_{10mbar}$=93° C. are obtained.

Smell: fresh, bergamot, grapefruit

Use Example

|  | A<br>Parts by weight | B<br>Parts by weight |
| --- | --- | --- |
| Bergamott Identoil colourless ® (H + R) | 175 | 175 |
| Dihydromyrcenol | 200 | 200 |
| Lemon oil | 100 | 100 |
| Vertocitral ® (H + R) | 5 | 5 |
| Methyl dihydrojasmonate | 50 | 50 |
| Citrophoral Supra ® (H + R) | 5 | 5 |
| Lavandin oil, Grosso | 25 | 25 |
| Oil of clary sage, French | 10 | 10 |
| Geranium Chin. Synthessence ® (H + R) | 30 | 30 |
| Damascon Beta ® (Firmenich) | 1 | 1 |
| Precyclemone B ® (IFF) | 19 | 19 |
| Isoananat ® (H + R) | 15 | 15 |
| Sandolen H & R ® (H + R) | 5 | 5 |
| Cedrylketon ® (H + R) | 100 | 100 |
| Chromanolid 50% in DEP ® (H + R) | 100 | 100 |
| Evernyl ® (Givauden Roure) | 10 | 10 |
| Ambroxid pure ® (H + R) | 10 | 10 |
| Dipropylene glycol | 140 | 100 |
| 2,2,5-Trimethyl-hex-4-en-1-ol formate | — | 40 |

DEP = diethyl phthalate

An unmistakable fresh green peak is caused in the tart composition by the addition of 2,2,5-trimethyl-hex-4-en-1-ol formate.

We claim:

1. Compounds of the formula

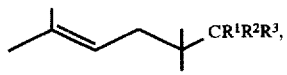  (I)

wherein $R^1$ denotes

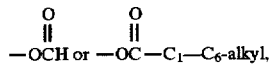

$R^2$ denotes hydrogen or $C_1$–$C_6$-alkyl and
$R^3$ denotes hydrogen or $C_1$–$C_4$-alkyl.

2. Compounds according to claim 1, wherein
$R^1$ denotes

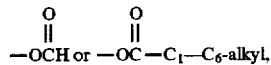

$R^2$ denotes hydrogen or $C_1$–$C_4$-alkyl and
$R^3$ denotes hydrogen, methyl or isopropyl.

3. In a method of preparing an aroma composition the improvement which comprises employing a compound according to claim 1.

* * * * *

UNITED STATES PATENT AND TRADEMARK OFFICE
CERTIFICATE OF CORRECTION

PATENT NO : 5,756,821
DATED : May 26, 1998
INVENTOR(S): Dilk, et al.

It is certified that error appears in the above-identified patent and that said Letters Patent is hereby corrected as shown below:

Col. 6, line 20   After " or " delete formula and substitute

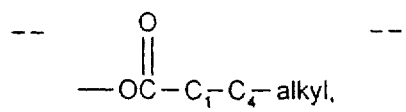

Signed and Sealed this

Eighth Day of June, 1999

Attest:

Q. TODD DICKINSON

Attesting Officer        Acting Commissioner of Patents and Trademarks